United States Patent [19]

Allegrini et al.

[11] Patent Number: 6,103,931
[45] Date of Patent: Aug. 15, 2000

[54] PROCESS FOR PREPARING (R)-2-BROMO-3-PHENYL-PROPIONIC ACID

[75] Inventors: Pietro Allegrini, Lonigo; Giorgio Soriato, S.Martino Buon Albergo, both of Italy

[73] Assignee: Zambon Group S.p.A., Vicenza, Italy

[21] Appl. No.: 09/251,432

[22] Filed: Feb. 17, 1999

[30]  Foreign Application Priority Data

Feb. 18, 1998 [IT] Italy .................................. MI98A0302

[51] Int. Cl.[7] .................... C07C 153/09; C07C 149/437
[52] U.S. Cl. .......................... 562/496; 562/426; 562/556; 562/557
[58] Field of Search ..................... 562/496, 602

[56]  References Cited

U.S. PATENT DOCUMENTS

| | | | |
|---|---|---|---|
| 4,339,600 | 7/1982 | Ondetti et al. ........................... | 562/426 |
| 5,238,932 | 8/1993 | Flynn et al. ............................. | 514/214 |
| 5,366,973 | 11/1994 | Flynn et al. ............................. | 514/221 |
| 5,504,080 | 4/1996 | Karanewsky ............................ | 514/214 |
| 5,508,272 | 4/1996 | Robl ........................................ | 514/80 |

FOREIGN PATENT DOCUMENTS

| | | |
|---|---|---|
| 524 553 A1 | 1/1993 | European Pat. Off. . |
| 657 453 A1 | 6/1995 | European Pat. Off. . |
| 56-158732 | 5/1980 | Japan . |

OTHER PUBLICATIONS

"Preparation of a–Bromo–and–a–Chlorocarboxylic Acids from a–Amino Acids[1])"; George Olah et al.; Helvetica Chimica Acta, vol. 66, Fasc. 4, (1983) pp. 1028–1030.

"Optimal Recognition of Neutral Endopeptidase and Angiotensin–Converting Enzyme Active Sites by Mercaptoacyl-dipeptides as a Means to Design Potent Dual Inhibitors" Pascale Coric et al.; J. Med. Chem. 1996, vol. 39, pp. 1210–1219.

"Design of Orally Active Dual Inhibitors of Neutral Endopeptidase and Angiotensin–Converting Enzyme with Long Duration of Action", Marie–Claude Fournie–Zaluski et al.; J. Med. Chem. 1996, vol. 39, pp. 2594–2608.

Synthesis of $C_2$–Symmetric HIV Protoase Inhibitors With Sulfur–Containing Control Units; Andrew Spaltenstein et al.; Tetrahedron Letters, vol. 34, No. 9, pp. 1457–1460. 1993.

H. Inoue et al., "A New Enantioselective Synthesis of (2R, 3S) –3–(4–methoxyphenyl) Glycidic Ester via the Enzymatic Hydrolysis of Erythro–N–Acetyl–Beta–(4–MethoxyphenylSerine", *Chemical & Pharmaceutical Bulletin*, vol. 41, No. 9, Sep. 1993, pp. 1521–1523.

*Primary Examiner*—Ardin H. Marschel
*Assistant Examiner*—Sherif Kafafi
*Attorney, Agent, or Firm*—Arent, Fox Kintner Plotkin & Kahn

[57]  ABSTRACT

It is described a process for preparing (R)-2-bromo-3-phenyl-propionic acid starting from (D)-phenyl-alanine, sodium nitrite and concentrated hydrobromic acid in a mixture of an aqueous solvent and a solvent selected from the group consisting of halogenated hydrocarbons and aromatic hydrocarbons.

11 Claims, No Drawings

PROCESS FOR PREPARING (R)-2-BROMO-3-PHENYL-PROPIONIC ACID

The present invention relates to a process for preparing (R)-2-bromo-3-phenyl-propionic acid. (R)-2-Bromo-3-phenyl-propionic acid is an intermediate useful in the preparation of many substances, specially in the synthesis of ACE/NEP inhibitors. See, for example, the patent application EP-0 524 553 (in the name of I.N.S.E.R.M.) which describes antihypertensive acylmercaptoalkanoylpeptides, the patent U.S. Pat. No. 4,339,600 (in the name of Squibb & Sons) relating to antihypertensive mercaptoacyl amino acids, the patents U.S. Pat. No. 5,504,080 and U.S. Pat. No. 5,508,272 (both in the name of Bristol-Myers Squibb) claiming ACE/NEP inhibitors.

As far as we know, one of the most common synthetic routes to (R)-2-bromo-3-phenyl-propionic acid consists in inserting a bromine atom in (D)-phenyl-alanine. As for the reaction in question as both reported by the prior art and discussed in the present invention the meaning of mole is equal to the one of equivalent.

The just cited patent application EP-0 524 553 shows the reaction between (D)-phenyl-alanine and 48% hydrobromic acid 1:1 v/v in water which is added with sodium nitrite, at a temperature of 0–20° C. for 3 hours overall. The product, i.e. (R)-2-bromo-3-phenyl-propionic acid, is extracted in ethyl ether with a yield of 60%.

The patents U.S. Pat. No. 5,238,932 and U.S. Pat. No. 5,366,973 illustrate the synthesis of (R)-2-bromo-3-phenyl-propionic acid starting from (D)-phenyl-alanine, 49% hydrobromic acid (in a ratio of 2:1 mole of amino acid) and sodium nitrite in water. The reaction is effected in the range from –5° C. to 0° C. for 5 hours, and the product is extracted in ethyl ether with a yield of 43%.

The patent application EP-0 657 453 (in the name of Bristol-Myers Squibb) describes the synthesis of (R)-2-bromo-3-phenyl-propionic acid starting from (D)-phenyl-alanine which is treated with sodium nitrite and potassium bromide in 2N sulfuric acid in water at 0° C., then at room temperature for 3 hours overall. The yield is of about 62%.

Olah G. A. et al., Helvetica Chimica Acta, 66, 4, No.101, 1028, 1983 describe the preparation of 2-halo-carboxyl acids, among which 2-bromo-3-phenyl-propionic acid is listed, starting from phenyl-alanine which is treated with a mixture of hydrofluoric acid/pyridine 7:3 by weight, potassium bromide and sodium nitrite, the two latter being in a double molar amount with respect to the amino acid, for about 48 hours in water. The product is extracted in ethyl ether and the yield is of 81%. It is apparent that due to the use of hydrofluoric acid, a highly scalding substance, this method may be hardly taken into consideration for an industrial application.

Coric P. et al., J.Med.Chem., 39, 1210–1219, 1996 illustrate a general synthetic scheme for 2-bromo alkanoic acids, among which 2-bromo-3-phenyl-propionic acid too. The synthesis starts from the due amino acid which is dissolved in 48% hydrobromic acid (8 equivalents versus 1 of amino acid) in water (2:3 v/v) at 0° C., then added with sodium nitrite (3.2 equivalents versus 1 of amino acid). The reaction goes on for 2 hours and the product is extracted in ethyl ether (yield: 88%).

Fournie-Zaluski M-C. et al., J.Med.Chem., 39, 2594–2608, 1996 describe in outline the synthesis of optically active 2-bromo alkanoic acids, among which 2-bromo-3-phenyl-propionic acid, starting from the due amino acid which is dissolved in 47% hydrobromic acid (8 equivalents versus 1 of amino acid) in water (2/3 v/v) at 0° C., then treated with sodium nitrite (6.5 equivalents versus 1 of amino acid). The article does not make notice of the yields of the product obtained.

The strong excess of sodium nitrite employed in the reactions described by these two latter references causes the generation of toxic vapours which make difficult the industrial application of these processes.

Spaltenstein A. et al., Tetrahedron Letters, 34, No.9, 1457–1460, 1993 illustrate the synthesis of 2-bromo-3-phenyl-propionic acid starting from phenyl-alanine which is treated with sodium nitrite, 2M sodium bromide and aqueous hydrobromic acid at room temperature for 3 hours with a yield of 80%. The ratios among the employed reactants is not specified.

It has been now surprisingly found a new synthetic method for (R)-2-bromo-3-phenyl-propionic acid, industrially applicable and profitable which allows to obtain the product with very good yield and in addition permits to use a less amount of reactants.

Therefore the present invention relates to a process for preparing (R)-2-bromo-3-phenyl-propionic acid starting from (D)-phenyl-alanine, sodium nitrite and concentrated hydrobromic acid in aqueous solvent at a temperature comprised between –10 and 0° C., under nitrogen, characterized in that the reaction is effected in the presence of a solvent selected from the group consisting of halogenated hydrocarbons and aromatic hydrocarbons.

Specific example of aromatic hydrocarbons are xylene, benzene and toluene.

Specific examples of halogenated hydrocarbons are methylene chloride, chlorobenzene, orthodichlorobenzene, 1,1,1-trichloro-ethane, 1,2-dichloro-ethane.

The process of the present invention is preferably effected in toluene.

The amount of the above said organic solvent useful to the scope of the present invention is generally comprised between 0.3 g and 5 g, preferably between 1 g and 2 g per gram of (D)-phenyl-alanine.

The hydrobromic acid is used in excess, preferably from 4 to 8 moles as compared to (D)-phenyl-alanine. The sodium nitrite is used in a virtually stoichiometric amount or in slight excess, preferably from 1 to 1.5 moles as compared to (D)-phenyl-alanine.

The preferred molar ratios in the range of the present invention provide the use of hydrobromic acid in an amount of 4 moles with respect to the amino acid, and of sodium nitrite in an amount of 1.3 moles always with respect to the amino acid.

It is meaningful that the process of the present invention allows to obtain the desired product in practically quantitative yields though using significantly lower amounts of reactant, i.e. hydrobromic acid, in comparison to the prior art.

(R)-2-Bromo-3-phenyl-propionic acid is thus directly isolated from the reaction medium by separating the organic phase and optional further extraction.

The particular and specific conditions which the synthesis object of the present invention is effected at, allow to obtain the product with yield equal or higher than 90%, to maintain the desired optical configuration and moreover to increase the productivity in comparison with the previous methods, productivity meaning the amount of final product isolated per litre of reaction mixture in the most diluted step of the process.

For better illustrating the present invention the following example is now provided.

EXAMPLE

In a 3 l jacketed reactor equipped with mechanical stirring and thermometer, 48% HBr (1,224.6 g, 7.265 moles), demineralized water (450 ml) and toluene (504 ml) were charged at 15° C. under nitrogen flow. The mixture temperature was brought to 0° C. and (D)-phenyl-alanine (300 g, 1.816 moles) was added. The mixture was then cooled to inner −5° C. and, in 5 hours, a solution of sodium nitrite (162.9 g, 2.361 moles) in demineralized water (306 ml) was dropped therein, keeping the temperature between −4° C. and −6° C. After 3 hours the reaction temperature was brought to 15° C. and the stirring was kept on for another hour, then the reaction mixture was left to stand for half of hour, the nitrogen flow was stopped and the phases were separated. The organic phase was added with toluene (800 g, 924 ml) and demineralized water (450 g). The mixture was stirred for 1 hour, left to stand for half of hour, and the phases separated. The organic one was concentrated to dryness under vacuum in thermostated bath at 50° C. There were thus obtained 385.8 g (1.684 moles) of (R)-2-bromo-3-phenylpropionic acid (yield: 92.7%).

What is claimed is:

1. Process for preparing (R)-2-bromo-3-phenyl-propionic acid starting from (D)-phenyl-alanine, sodium nitrite and concentrated hydrobromic acid in aqueous solvent at a temperature comprised between −10° C. and 0° C. under nitrogen characterized in that the reaction is effected in the presence of a solvent selected from the group consisting of halogenated hydrocarbons and aromatic hydrocarbons.

2. Process according to claim 1 wherein the aromatic hydrocarbons are xylene, benzene and toluene.

3. Process according to claim 1 wherein the halogenated hydrocarbons are methylene chloride, chlorobenzene, orthodichlorobenzene, 1,1,1-trichloro-ethane, 1,2-dichloro-ethane.

4. Process according to claim 1 wherein the reaction is effected in the presence of toluene.

5. Process according to claim 1 wherein the amount of organic solvent is comprised between 0.3 g and 5 g per gram of (D)-phenyl-alanine.

6. Process according to claim 1 wherein the amount of organic solvent is comprised between 1 g and 2 g per gram of (D)-phenyl-alanine.

7. Process according to claim 1 wherein hydrobromic acid is used in excess with respect to (D)-phenyl-alanine.

8. Process according to claim 1 wherein hydrobromic acid is used in an amount of from 4 to 8 moles with respect to (D)-phenyl-alanine.

9. Process according to claim 1 wherein hydrobromic acid is used in an amount of 4 with respect to (D)-phenyl-alanine.

10. Process according to claim 1 wherein sodium nitrite is used in an amount of from 1 to 1.5 moles with respect to (D)-phenyl-alanine.

11. Process according to claim 1 wherein sodium nitrite is used in an amount of 1.3 moles with respect to (D)-phenyl-alanine.

* * * * *